United States Patent
Goi

(10) Patent No.: US 8,799,669 B2
(45) Date of Patent: *Aug. 5, 2014

(54) SAFETY MANAGEMENT SYSTEM

(75) Inventor: Kouichi Goi, Kawasaki (JP)

(73) Assignee: Laurel Precision Machines Co., Ltd., Osaka (JP)

(*) Notice: Subject to any disclaimer, the term of this patent is extended or adjusted under 35 U.S.C. 154(b) by 1270 days.

This patent is subject to a terminal disclaimer.

(21) Appl. No.: 12/149,719

(22) Filed: May 7, 2008

(65) Prior Publication Data
US 2008/0295152 A1    Nov. 27, 2008

(30) Foreign Application Priority Data

May 25, 2007 (JP) ................. P2007-139197

(51) Int. Cl.
*H04L 29/06* (2006.01)
(52) U.S. Cl.
USPC ........................... 713/186; 726/2
(58) Field of Classification Search
CPC ........... A61B 5/117; A61B 5/14532; A61B 5/14546; A61B 5/1455; G06K 2009/00932; G07C 9/00158; G06F 21/32; H04L 9/0866; H04L 9/3231; H04L 63/0861
USPC ............................ 726/2; 713/186
See application file for complete search history.

(56) References Cited

U.S. PATENT DOCUMENTS

| | | | |
|---|---|---|---|
| 3,508,830 A | 4/1970 | Hopkins et al. | |
| 4,035,083 A | 7/1977 | Woodriff et al. | |
| 5,303,575 A * | 4/1994 | Brown et al. | 73/23.3 |
| 5,589,045 A * | 12/1996 | Hyodo | 702/19 |
| 5,719,950 A * | 2/1998 | Osten et al. | 382/115 |
| 6,097,480 A * | 8/2000 | Kaplan | 356/139 |
| 6,216,032 B1 * | 4/2001 | Griffin et al. | 600/515 |
| 6,229,908 B1 | 5/2001 | Edmonds et al. | |
| 6,313,749 B1 * | 11/2001 | Horne et al. | 340/575 |
| 6,726,636 B2 * | 4/2004 | Der Ghazarian et al. | 600/532 |
| 6,748,301 B1 | 6/2004 | Ryu | |
| 6,886,653 B1 * | 5/2005 | Bellehumeur | 180/272 |
| 7,103,460 B1 * | 9/2006 | Breed | 701/32.9 |
| 7,203,345 B2 | 4/2007 | Rowe et al. | |

(Continued)

FOREIGN PATENT DOCUMENTS

| | | |
|---|---|---|
| DE | 202005020535 U1 | 4/2006 |
| EP | 1 703 045 | 9/2006 |

(Continued)

OTHER PUBLICATIONS

Office Action dated Dec. 6, 2010 issued in U.S. Appl. No. 12/149,897, 9 pp.

(Continued)

*Primary Examiner* — David Garcia Cervetti
(74) *Attorney, Agent, or Firm* — Nixon & Vanderhye P.C.

(57) ABSTRACT

A safety management system includes a user authentication section which authenticates a user of a particular facility and outputs an authentication result, and a health status determination section which measures blood component data of a user authenticated by the user authentication section. The health status determination section determines a health status of the user from the blood component data and outputs a determination result. An entry regulating section permits or prohibits entry by the user to the particular facility based on the authentication result and the determination result.

4 Claims, 2 Drawing Sheets

(56) References Cited

U.S. PATENT DOCUMENTS

| | | | |
|---|---|---|---|
| 7,248,905 B2* | 7/2007 | Fukuda et al. | 600/310 |
| 7,298,874 B2* | 11/2007 | Cho | 382/118 |
| 7,386,152 B2 | 6/2008 | Rowe et al. | |
| 7,885,434 B2* | 2/2011 | Kitane et al. | 382/115 |
| 7,913,090 B2* | 3/2011 | Abe | 713/186 |
| 2002/0084130 A1* | 7/2002 | Der Ghazarian et al. | 180/272 |
| 2003/0012374 A1* | 1/2003 | Wu et al. | 380/44 |
| 2003/0084288 A1* | 5/2003 | de Jong et al. | 713/168 |
| 2003/0084302 A1* | 5/2003 | de Jong et al. | 713/185 |
| 2003/0100841 A1* | 5/2003 | Griffin et al. | 600/515 |
| 2003/0204290 A1 | 10/2003 | Sadler et al. | |
| 2004/0035423 A1* | 2/2004 | Platt et al. | 128/204.23 |
| 2004/0039297 A1* | 2/2004 | Abreu | 600/558 |
| 2004/0114782 A1* | 6/2004 | Cho | 382/117 |
| 2004/0220483 A1* | 11/2004 | Yeo et al. | 600/500 |
| 2004/0240712 A1* | 12/2004 | Rowe et al. | 382/124 |
| 2005/0087382 A1* | 4/2005 | Bellehumeur | 180/272 |
| 2005/0192493 A1* | 9/2005 | Wuori | 600/322 |
| 2005/0254690 A1* | 11/2005 | Nagasaka et al. | 382/115 |
| 2005/0275550 A1* | 12/2005 | Wang et al. | 340/632 |
| 2005/0286744 A1* | 12/2005 | Yoshizu et al. | 382/115 |
| 2006/0023919 A1* | 2/2006 | Okamura et al. | 382/115 |
| 2006/0048212 A1* | 3/2006 | Tsuruoka et al. | 726/4 |
| 2006/0072793 A1* | 4/2006 | Determan | 382/117 |
| 2006/0078170 A1* | 4/2006 | Kamata et al. | 382/115 |
| 2006/0080547 A1* | 4/2006 | Higashiura et al. | 713/186 |
| 2006/0180371 A1* | 8/2006 | Breed et al. | 180/197 |
| 2006/0217615 A1* | 9/2006 | Huiku et al. | 600/484 |
| 2006/0224171 A1* | 10/2006 | Sakata et al. | 606/181 |
| 2006/0284839 A1* | 12/2006 | Breed et al. | 345/156 |
| 2007/0003112 A1* | 1/2007 | Awatsu et al. | 382/115 |
| 2007/0037554 A1* | 2/2007 | Freeny, Jr. | 455/410 |
| 2007/0067330 A1* | 3/2007 | Hernandez et al. | 707/102 |
| 2007/0092924 A1* | 4/2007 | Anderson | 435/23 |
| 2007/0260887 A1* | 11/2007 | Ito | 713/186 |
| 2008/0130962 A1* | 6/2008 | Lee et al. | 382/118 |
| 2008/0176305 A1* | 7/2008 | Sato et al. | 435/170 |
| 2009/0240119 A1* | 9/2009 | Schwaibold et al. | 600/301 |
| 2010/0008545 A1* | 1/2010 | Ueki et al. | 382/115 |
| 2010/0010689 A1* | 1/2010 | Yasushi et al. | 701/1 |

FOREIGN PATENT DOCUMENTS

| | | |
|---|---|---|
| JP | 2001-258867 | 9/2001 |
| JP | 2002-172105 | 6/2002 |
| JP | 2003-146107 | 5/2003 |
| JP | 2005-202899 | 7/2005 |
| JP | 2006-6762 | 1/2006 |
| JP | 2006-248254 | 9/2006 |
| JP | 2006-291604 | 10/2006 |
| JP | 2007-23526 | 2/2007 |
| JP | 2007-097820 | 4/2007 |
| JP | 2007-117221 | 5/2007 |
| TW | I254254 | 5/2006 |
| WO | WO 99/32317 | 7/1999 |
| WO | WO 2008/019800 A1 | 2/2008 |

OTHER PUBLICATIONS

Office Action dated Aug. 8, 2011 issued in U.S. Appl. No. 12/149,897, 14 pp.

Office Action dated Oct. 4, 2011 issued in Japanese Patent Application No. 2007-136579 with translation, 6 pp.

Office Action dated Nov. 22, 2011 issued in Japanese Patent Application No. 2007-139197 with translation, 4 pp.

Notice of Allowance dated May 29, 2012 issued in Japanese Patent Application No. 2007-136579, 6 pp.

Office Action dated Mar. 12, 2012 issued in U.S. Appl. No. 12/149,897, 16 pp.

Office Action dated Feb. 16, 2012, issued in Taiwanese Patent Application No. 097117333, with English Translation, 7 pp.

* cited by examiner

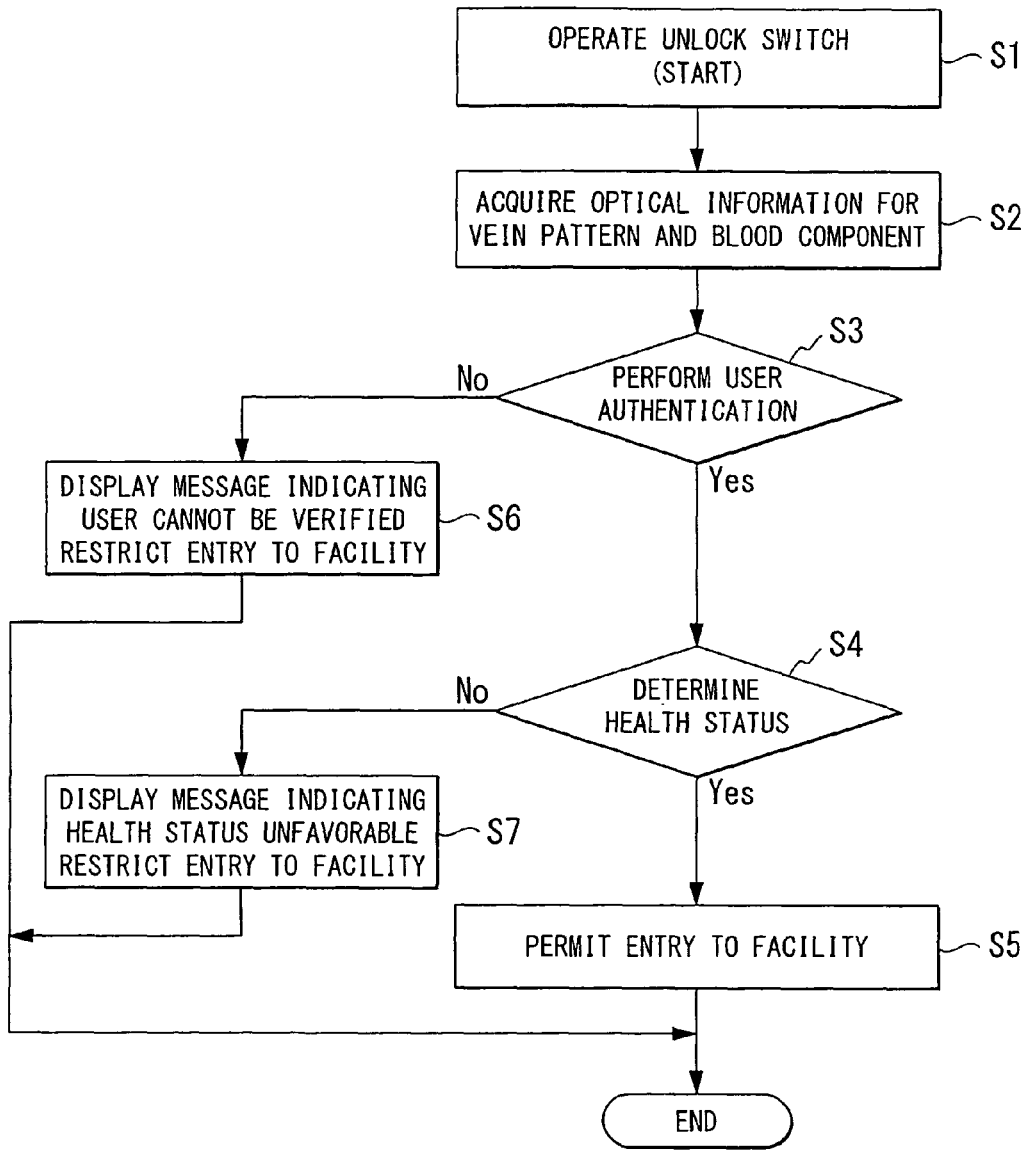

US 8,799,669 B2

SAFETY MANAGEMENT SYSTEM

BACKGROUND OF THE INVENTION

1. Field of the Invention

The present invention relates to a safety management system which prohibits entry by unauthorized persons to a particular facility such as an aircraft control room or reactor control room.

Priority is claimed on Japanese Patent Application No. 2007-139197, filed May 25, 2007, the contents of which are incorporated herein by reference.

2. Description of the Related Art

Japanese Unexamined Patent Application, First Publication No. 2007-23526 discloses that entry to a controlled area of a particular facility from outside is managed according to ID information entered by users, and exit from inside the controlled area to outside the controlled area is managed according to biological information of the user, allowing entry and exit to be managed with a high level of security.

The technology described above enhances security by restricting unauthorized persons from exiting the controlled area. However, in particular facilities such as aircraft control rooms or reactor control rooms, the operation of equipment by unauthorized persons must also be prevented by such means as restricting their entry. Furthermore, even in the case of an authorized person, the health status of that person may increase the probability of erroneous operation. Consequently, there is a need for a configuration in which entry to a particular facility is permitted or prohibited subject to checking the health status of the user, and operation of the equipment inside the particular facility by the user can be permitted or prohibited conditional upon whether the health status of the user is favorable.

SUMMARY OF THE INVENTION

An object of the present invention is to provide a safety management system that prohibits the entry of unauthorized persons to a particular facility, in which the health status of the user is reflected on to permit or prohibit entry to the particular facility.

In order to solve the above problem, the safety management system of the present invention comprises: a user authentication section which authenticates a user of a particular facility and outputs an authentication result; a health status determination section which measures blood component data of a user authenticated by the user authentication section, determines a health status of the user from the blood component data, and outputs a determination result; and an entry regulating section which permits or prohibits entry by the user to the particular facility based on the authentication result and the determination result.

According to this configuration, a legitimate user is authenticated. Furthermore, based on the blood component data of that user it is determined whether or not the health status of a user is favorable, and based on the result entry to the particular facility is permitted or prohibited. Consequently, operation of the equipment inside the particular facility by the user can be permitted or prohibited.

In the safety management system of the present invention, the entry regulating section may permit or prohibit entry to the particular facility according to whether values of each of items of the blood component data are within predetermined ranges.

In the safety management system of the present invention, the entry regulating section may permit or prohibit entry to the particular facility according to whether values of each of specific items of the items of the blood component data are within predetermined ranges.

In the safety management system of the present invention, the entry regulating section may permit or prohibit entry to the particular facility according to a number of items within the predetermined ranges of each of the items of the blood component data.

In the safety management system of the present invention, the user authentication section may authenticate the user based on a vein pattern obtained by irradiating infrared rays onto a body of the user.

In the safety management system of the present invention, the health status determination section may measure the blood component data based on an absorption spectrum obtained by irradiating infrared rays onto a body of the user.

According to this configuration, because blood component data is measured in a non-invasive manner, the physical and mental stress experienced by the user can be minimized.

In the safety management system of the present invention, a vein pattern used by the user authentication section and an absorption spectrum used by the health status determination section may be detected by the same sensor section.

According to this configuration, user authentication and health status determination can be performed in the same operation, and the structure of the overall system can be simplified.

The safety management system of the present invention may further comprise, in addition to or instead of the entry regulating section, an operation regulating section which permits or prohibits operation of equipment inside the particular facility based on the authentication result and the determination result.

According to this configuration, in addition to or instead of permitting or prohibiting entry to the particular facility, by switching between states in which the user can and cannot operate the equipment inside the particular facility or switching between states in which such operations are valid or invalid, operation of the equipment can be permitted or restricted. As a result, safety management that is as reliable as or more reliable than a system that permits or prohibits entry can be achieved.

According to the present invention, a legitimate user is authenticated, the health status of the user is determined based on blood component data, and entry to the particular facility is permitted or prohibited based on the result (operation of the equipment inside the particular facility is permitted or prohibited). As a result, the likelihood of a user, due to poor health, performing an erroneous operation that leads to an accident can be reduced.

BRIEF DESCRIPTION OF THE DRAWINGS

FIG. 2 is a flowchart showing the process flow of the safety management system shown in FIG. 1.

DETAILED DESCRIPTION OF THE INVENTION

Figure 1:
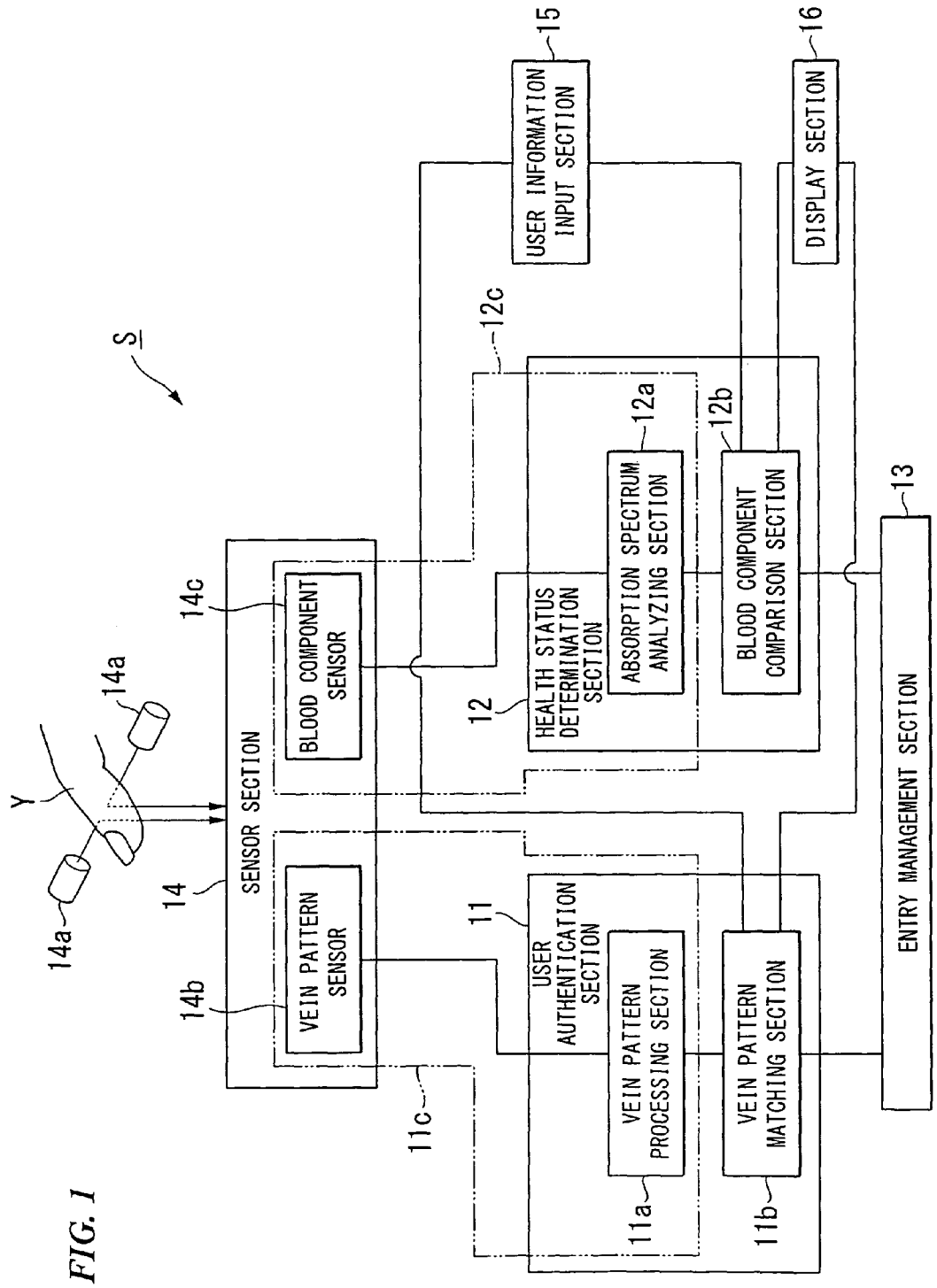
FIG. 1 is a block diagram showing a safety management system according to an embodiment of the invention.

As follows is a description of an embodiment of the present invention with reference to the drawings.

A safety management system S shown in FIG. 1 is used in a particular facility, such as an aircraft control room or reactor control room, where entry to a controlled area is managed. The safety management system S performs authentication to determine whether a user is a pre-registered user, and also checks the health status of that user. Based on the results, the safety management system S regulates entry to the particular facility by permitting or prohibiting entry by the user.

The safety management system S includes a user authentication section 11, a health status determination section 12, and an entry management section 13. The user authentication section 11 performs authentication to determine whether or not a user is a legitimate user. The health status determination section 12 determines the health status of the user from blood component data of the user. The entry management section 13 manages (permits or prohibits) the entry of the user to the particular facility based on the authentication result of the user authentication section 11 and the judgment result of the health status determination section 12. The user authentication section 11, the health status determination section 12, and the entry management section 13 are formed inside an electronic control unit which controls the overall operation of the particular facility.

The user authentication section 11 is a known vein authentication device. The user authentication section 11 acquires a vein pattern from, for example, the fingertip of the user, and matches the vein pattern to a pre-registered vein pattern. The user authentication section 11, based on the results of the matching process, determines whether or not the user is permitted entry, that is, the user authentication section 11 determines whether the user is a legitimate user. The vein pattern is acquired, for example, in the following manner. A user places his or her fingertip Y on a sensor section 14 positioned near the entrance to the particular facility. An infrared LED 14a irradiates near-infrared light onto the fingertip Y, and the reflected light is received by an imaging element such as a CCD (charge coupled device). A vein pattern processing section 11a of the user authentication section 11 performs predetermined image processing of the signal from the imaging element. This vein pattern processing section 11a and a vein pattern sensor 14b of the sensor section 14 constitute a vein pattern capture section 11c in the user authentication section 11.

A user information input section 15 is a keyboard or card reader or the like. A vein pattern matching section 11b of the user authentication section 11, based on information from the user information input section 15, retrieves a pre-registered vein pattern of the user.

The vein pattern matching section 11b compares the retrieved vein pattern with the vein pattern obtained by the sensor section 14. If the vein pattern matching section 11b determines that the two vein patterns are the same, the user is authenticated as a legitimate user (in which case the "authentication result is OK"). On the other hand, if the vein pattern matching section 11b determines that the two vein patterns are not the same, the user is not authenticated as a legitimate user (in which case the "authentication result is NG"). These authentication results are displayed to the user on a predetermined display section 16 such as an LCD (liquid crystal display). A configuration may also be used in which the user information input section 15 is not provided, and user authentication is performed by automatically comparing the vein pattern acquired by the sensor section 14 with pre-registered vein patterns.

As the health status determination section 12, a known non-invasive blood component measuring device is used. The health status determination section 12 analyzes an absorption spectrum obtained from transmitted or reflected light obtained by irradiating near-infrared rays onto the fingertip Y of the user in the sensor section 14. From the results of analyzing this absorption spectrum, the health status determination section 12 acquires data (blood component data) related to the blood components of that user. An absorption spectrum analyzing section 12a of the health status determination section 12 analyzes the absorption spectrum. This absorption spectrum analyzing section 12a and a blood component sensor 14c of the sensor section 14 constitute a blood component measuring section 12c in the health status determination section 12. The blood component measuring section 12c utilizes an infrared spectrophotometer.

Items of blood components measured by the health status determination section 12 include blood sugar levels, levels of enzymes such as GPT (glutamic pyruvic transaminase), levels of plasma proteins such as albumin, and cholesterol levels and lactic acid levels.

A blood component comparison section 12b of the health status determination section 12 retrieves blood component data values (the "predetermined ranges" mentioned below) registered in advance for each item of the blood data, which indicate the appropriate health status of the user for operating the equipment inside the particular facility.

The blood component comparison section 12b compares the retrieved blood component data values with the blood component data obtained by analyzing the absorption spectrum. From the comparison results, the blood component comparison section 12b then determines whether the health status of the user is suitable for operating the equipment inside the particular facility.

Specifically, the blood component comparison section 12b pre-designates several items in the blood component data as the specific items. The specific items are, for example, the plasma protein level and the lactic acid level which indicate the level of tiredness of the user. The blood component comparison section 12b determines whether or not the values of the specific items in the measured blood component data are within the value of the retrieved blood component data, that is, the blood component comparison section 12b determines whether the values are within the predetermined ranges for each of the specific items. These predetermined ranges are ranges whereby a determination can be made as to whether the health status of the user is appropriate for operating the equipment inside the particular facility. These predetermined ranges can be set appropriately based on the age and gender of the user as well as individual differences. A construction may be employed in which the predetermined ranges are appropriately corrected or updated based on blood component data acquired in the past.

If the blood component comparison section 12b determines that the values of all the specific items are within their predetermined ranges (all items meet the required standard), the health status of the user is determined to be suitable for operating equipment inside the particular facility, that is, the health status of the user is determined to be favorable (in which case the "authentication result is OK"). On the other hand, if the blood component comparison section 12b determines that the value of one or more of the specific items is outside the predetermined range defined for the item (at least one item does not meet the required standard), the health status of the user is determined to not be suitable for operating equipment inside the particular facility, that is, the health status of the user is determined not to be favorable (in which case the "authentication result is NG"). These determination results are displayed to the user on the display section 16.

The entry management section 13 controls the entry of users into the particular facility, by such means as locking and unlocking the entry door to the particular facility. Specifically, when the authentication result of the user authentication section 11 and the judgment result of the health status determination section 12 are both OK, the entry management section 13 unlocks the entry door. On the other hand, if at least the authentication result of the user authentication section 11 or the judgment result of the health status determination section 12 is NG, the entry management section 13 leaves the entry door locked.

In this manner, by authenticating a user and also determining whether or not the health status of the user is favorable (whether or not the health status of the user is suitable for operating equipment inside the particular facility), and controlling entry to the particular facility according to the results, users other than users who have been granted permission in advance are prevented from entering the particular facility, and incidents in which, due to poor health, a user performs an erroneous operation and causes an accident can be prevented beforehand. A construction may be employed in which the method of managing entry, rather than locking or unlocking the entry door, involves opening the entry door automatically only when both the authentication results and judgment results are OK.

Next, the main process flow of the safety management system S is described with reference to FIG. 2.

First, the process flow starts when a user, before entering, operates the unlock switch located near the entry door (step S1). The unlock switch is, for example, a push-button switch, on the top face of which the user places his or her fingertip. A pair of infrared LEDs 14a are provided on either side of the unlock switch so as to face each other. This unlock switch and the infrared LEDs 14a constitute the sensor section 14. The unlock switch also incorporates a light receiving section. By receiving the light emitted by the LEDs 14a after the light has passed through the fingertip Y of the user, the light receiving section acquires optical information related to the vein pattern of the fingertip Y of the user and the blood component data of the user (step S2). The unlock switch incorporates the vein pattern sensor 14b and the blood component sensor 14c of the sensor section 14.

The vein pattern processing section 11a subjects the optical information acquired by the vein pattern sensor 14b to predetermined image processing. Next, the vein pattern matching section 11b matches the image processed optical information to a pre-registered vein pattern. Specifically, the user authentication section 11 compares the vein pattern acquired by the sensor section 14 with a retrieved vein pattern. Based on the results of the comparison, the user authentication section 11 determines whether or not the user is a person who is permitted entry, that is, the user authentication section 11 determines whether or not the user is a legitimate user (step S3).

If a determination is made that the user is a person who is permitted entry, that is, if the authentication result is OK (YES in step S3), the processing proceeds to step S4. On the other hand, if a determination is made that the user is a person who is not permitted entry, that is, if the authentication result is NG (NO in step S3), the processing proceeds to step S6. In step S6, a message indicating that the user cannot be verified is displayed on the display section 16, and the entry management section 13 restricts entry by such means as not unlocking the entry door (prohibiting entry to the particular facility).

On the other hand, in step S4, the absorption spectrum analyzing section 12a subjects the optical information acquired by the blood component sensor 14c to predetermined analysis, and the blood component comparison section 12b then compares the results of the analysis with pre-registered blood component data. Specifically, the health status determination section 12 compares the values of blood component data acquired by the sensor section 14 and retrieved blood component data. Based on the comparison results, the health status determination section 12 determines whether or not the health status of the user is suitable for operating equipment inside the particular facility.

If a determination is made that the health status of the user is favorable, that is, if the judgment result is OK (YES in step S4), the processing proceeds to step S5. On the other hand, if a determination is made that the health status of the user is not favorable, that is, if the judgment result is NG (NO in step S4), the processing proceeds to step S7. In step S7, a message indicating that the health status of the user is not favorable is displayed on the display section 16, and the entry management section 13 restricts entry in the manner previously described.

In step S5, the entry management section 13 allows the user to enter by such means as unlocking the entry door. As a result, the user is able to operate the equipment inside the particular facility.

Although two infrared LEDs 14a are used in FIG. 1, a construction in which one infrared LED 14a is used may be employed. The unlock switch may be a lever or dial instead of a push-button switch. A construction may be used in which the unlock switch is rendered operable after the user has been authenticated and a determination has been made as to whether or not the health status of the user is favorable. In this construction, the unlock switch may be rendered operable only when the authentication result of the user authentication section 11 and the judgment result of the health status determination section 12 are both OK (that is, the unlock switch is rendered inoperable when any one of the authentication result and the judgment result are NG).

The sensor section 14 and the unlock switch may be provided as separate components. A construction may also be used in which the user places his or her fingertip Y in a predetermined enclosure to allow the sensor section 14 to capture a vein pattern and acquire blood component data. The sensor section 14 may also capture a vein pattern and acquire blood component data of the user using a different part of the body than the fingertip of the user, such as a finger or palm (a part of the body where blood flow can be readily observed).

As described above, the safety management system S in this embodiment prevents unauthorized persons from entering a particular facility. The safety management system S includes a user authentication section 11 which authenticates a user of a particular facility and outputs an authentication result, a health status determination section which measures the blood component data of the user authenticated by the user authentication section 11, determines the health status of the user from the blood component data, and outputs a determination result, the entry regulating section 13 which permits or prohibits entry by the user to the particular facility based on the authentication result and the determination result.

According to this configuration, a legitimate user is authenticated. Furthermore based on the blood component data of that user it is determined whether or not the health status of the user is favorable. Based on the results, entry to the particular facility is permitted or prohibited. As a result, operation of the equipment inside the particular facility by the user can be permitted or prohibited. Consequently the likelihood of a user, due to poor health, performing an erroneous operation that leads to an accident can be reduced.

In the safety management system S, the user authentication section 11 authenticates users based on a vein pattern obtained by irradiating infrared rays onto the body of the user. Therefore, authentication can be performed with similar accuracy to authentication using fingerprint or iris recognition. The health status determination section 12 measures the blood component data of the user based on an absorption spectrum obtained by irradiating infrared rays onto the body of the user. Thus, because the blood component data is measured in a non-invasive manner, the physical and mental stress experienced by the user can be minimized.

In the safety management system S, the vein pattern used by the user authentication section 11 and the absorption spectrum used by the health status determination section 12 are detected by a single sensor section 14. As a result, user authentication and user health status determination can be performed in the same operation, and the structure of the overall system can be simplified.

The present invention is not limited to the embodiment described above. For example, the health status determination section 12 may adopt the following configuration. That is to say, the health status determination section 12 assigns a predetermined range as the normal range for each item of the retrieved blood component data including those not designated as the specific items. The health status determination section 12 determines whether the values of all items including the specific items in the measured blood component data are within the predetermined ranges defined for each item in the retrieved blood component data. From the judgment results, the health status determination section 12 determines that the health status of the user is suitable for operating the equipment inside the particular facility when the values of all items are within their predetermined ranges or when the number of items within their predetermined ranges is equal to or greater than a predetermined number. In addition, based on the judgment results, the entry management section 13 permits the user entry to the particular facility. As a result, the user is able to operate the equipment inside the particular facility. At this time, a requirement may be that the values of all of the specific items are within their predetermined ranges.

A log creation section may be provided which creates logs of such information as the identity and health status of the user, and the date and time. At this time, some or all of the log information may be displayed on, for example, the screen of the display section 16. Log information may be displayed as numerical data, or in the form of a graph or the like. As a result, the user can monitor his or her health status on a daily basis.

If data that cannot be read by the sensor section 14 (such as the breath alcohol concentration of the user) is to be used as a condition for permitting or prohibiting entry, a detection device for obtaining the data can be incorporated into the safety management system, and entry by the user can be permitted or prohibited in light of this additional data.

Instead of the entry management section 13, the safety management system S may include an operation regulating section which permit or prohibit operation of the equipment inside the particular facility based on the authentication result of the user authentication section 11 and the judgment result of the health status determination section 12. The operation regulating section, according to the authentication result and the judgment result, for example, can render the various switches operable or inoperable by such means as operating covers installed on the equipment inside the particular facility. This operation regulating section may permit or prohibit the operation of equipment based on whether or not the health status of the user determined when he or she entered the facility was favorable. Alternatively, a configuration may be used in which an additional device which measures the blood component data and determines whether or not the health status of the user is favorable, is provided inside the particular facility, and the operation regulating section permits or prohibits operation based on the results. At this time, a construction may be employed in which the safety management system S includes both the operation regulating section and the entry management section 13, both of which permit or prohibit the operation of equipment. As a result, for example, if the physical condition of the user changes after he or she is granted permission to enter the particular facility, operation of the relevant equipment can be permitted or prohibited accordingly.

The safety management system S is suitable not only for the aircraft control rooms or reactor control rooms mentioned, but also for any facility that requires fast and accurate judgment, such as traffic control rooms or marine control rooms, or the control rooms and instrument rooms of all kinds of large scale industrial plants such as power stations or ironworks.

The blood component data may also be obtained by collecting a blood sample.

The construction of the embodiment described above is but one example of the present invention, and various modifications are possible provided that they do not depart from the scope of the present invention.

What is claimed is:

1. A safety management system comprising:
a sensor that irradiates infrared light onto a portion of skin of a user of a particular facility, the sensor receiving the light passed through the portion of the skin of the user, the sensor acquiring, from the received light, optical information related to a vein pattern of the portion of the skin of the user and blood component data of the user including a plasma protein level and a lactic acid level;
a user authentication section including a processor that processes the optical information to acquire the vein pattern, the user authentication section authenticating the user based on the vein pattern and outputting an authentication result;
a health status determination section including a processor that processes the optical information to acquire the blood component data of the user the health status determining section determining whether values of the plasma protein level and the lactic acid level in the blood component data measured by the health status determination section are within pre-registered blood component data values indicating an appropriate health status of the user for operating equipment inside the particular facility, and the health status determination section outputting a determination result, wherein the health status determination section is configured to correct ranges of the pre-registered blood component data values based on previously acquired blood component data of the user; and
an entry regulating section which permits or prohibits entry by the user to the particular facility based on the authentication result and the determination result.

2. A safety management system according to claim 1, further comprising, in addition to or instead of said entry regulating section, an operation regulating section which permits or prohibits operation of equipment inside the particular facility based on the authentication result and the determination result.

3. A safety management system according to claim 1, wherein the blood component data of the user consists of the plasma protein level and the lactic acid level.

4. A safety management system according to claim 1, wherein the pre-registered blood component data values are set based on an age and gender of the user and individual differences.

* * * * *